(12) United States Patent
Neumann

(10) Patent No.: US 11,593,679 B2
(45) Date of Patent: Feb. 28, 2023

(54) METHOD OF AND SYSTEM FOR GENERATING A LONGEVITY ELEMENT AND AN INSTRUCTION SET FOR A LONGEVITY ELEMENT PLAN

(71) Applicant: KPN Innovations, LLC, Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 311 days.

(21) Appl. No.: 16/890,628

(22) Filed: Jun. 2, 2020

(65) Prior Publication Data

US 2021/0166137 A1 Jun. 3, 2021

Related U.S. Application Data

(63) Continuation-in-part of application No. 16/699,407, filed on Nov. 29, 2019, now Pat. No. 10,734,096.

(51) Int. Cl.
*G06N 20/00* (2019.01)
*G06N 5/04* (2023.01)

(52) U.S. Cl.
CPC ............. *G06N 5/04* (2013.01); *G06N 20/00* (2019.01)

(58) Field of Classification Search
CPC ........ G06N 20/00; G16H 20/60; G16H 20/10; G16H 10/60; G06F 19/3475;
(Continued)

(56) References Cited

U.S. PATENT DOCUMENTS 5,954,640 A * 9/1999 Szabo ................... G16H 10/60
600/300
7,136,820 B1 * 11/2006 Petrus ................... G16H 20/60
600/300
(Continued)

FOREIGN PATENT DOCUMENTS

WO 2010030600 3/2010
WO 2018204763 11/2018
WO WO-2018204763 A2 * 11/2018 ............. G06Q 30/02

OTHER PUBLICATIONS

"Baze; Personalized Vitamins Based on a Convenient Blood Test"; Nov. 7, 2019; https://www.baze.com/how-it-works/ retrieved Nov. 7, 2019.
(Continued)

Primary Examiner — Paulinho E Smith
(74) Attorney, Agent, or Firm — Caldwell Intellectual Property Law

(57) ABSTRACT

A system for generating a longevity element and an instruction set for a longevity element plan, the system including at least a computing device, wherein the computing device is designed and configured to receive, from a user, at least an element of user-reported data, determine, using the at least an element of user-reported data and a first machine-learning process, a longevity element, calculate, using a longevity element and at least a second element of data, a compensatory supplement, and generate, using the at least an element of user-reported data and at least a longevity element, an instruction set for a longevity element plan.

20 Claims, 5 Drawing Sheets

(58) Field of Classification Search
CPC ............ G06F 16/9535; G06F 19/3456; G06Q 30/0269; G06Q 30/0631; G09B 19/0092
See application file for complete search history.

(56) References Cited

U.S. PATENT DOCUMENTS

| | | | | |
|---|---|---|---|---|
| 7,809,601 B2* | 10/2010 | Shaya | ................ | G06Q 30/0641 705/26.7 |
| 7,953,613 B2* | 5/2011 | Gizewski | ................ | G16H 40/60 705/2 |
| 10,332,418 B2* | 6/2019 | Hardee | ................ | G01N 33/0047 |
| 10,553,319 B1* | 2/2020 | Neumann | ................ | G06N 7/005 |
| 10,559,386 B1* | 2/2020 | Neumann | ................ | G16H 50/20 |
| 2003/0069757 A1* | 4/2003 | Greenberg | ............ | G16H 20/60 705/2 |
| 2005/0011804 A1* | 1/2005 | Zanden | .................... | A61J 7/04 206/534 |
| 2007/0143126 A1* | 6/2007 | Ghose | ................... | G16H 20/60 434/127 |
| 2007/0174088 A1* | 7/2007 | Koo | ...................... | G06Q 30/02 705/28 |
| 2008/0162352 A1* | 7/2008 | Gizewski | ............... | G16Z 99/00 705/50 |
| 2008/0275912 A1* | 11/2008 | Roberts | ................. | G16B 20/00 |
| 2010/0196483 A1* | 8/2010 | Muellinger | ........... | A61K 31/573 424/45 |
| 2011/0014351 A1* | 1/2011 | Reider | ................... | G16H 10/20 53/473 |
| 2011/0054928 A1* | 3/2011 | Sullivan | ................ | G16H 20/60 705/2 |
| 2013/0023058 A1* | 1/2013 | Toumazou | ............ | G16H 10/20 436/501 |
| 2013/0036075 A1* | 2/2013 | Kutzko | ................. | G16H 20/10 705/500 |
| 2014/0136362 A1* | 5/2014 | Shaya | .................... | G06Q 30/02 705/26.7 |
| 2014/0236759 A1* | 8/2014 | Mirabile | ............ | G06Q 30/0633 705/26.8 |
| 2015/0012295 A1* | 1/2015 | Mahoney | ............... | G16H 20/60 705/3 |
| 2016/0103977 A1* | 4/2016 | Mandel | .................. | G16H 20/17 705/2 |
| 2017/0098056 A1* | 4/2017 | Reddy | .................... | G16H 20/13 |
| 2017/0148348 A1* | 5/2017 | Hardee | ............. | G09B 19/0092 |
| 2017/0151265 A1* | 6/2017 | Kumar | ................... | A61K 31/52 |
| 2018/0144820 A1* | 5/2018 | Grimmer | ................ | A61P 25/18 |
| 2018/0211723 A1* | 7/2018 | Coles | ..................... | G16H 20/60 |
| 2019/0172575 A1* | 6/2019 | Reddy | ............... | H04M 1/72412 |
| 2019/0259482 A1* | 8/2019 | Puirava | .................. | G06N 20/00 |
| 2020/0000270 A1* | 1/2020 | Lotti | ..................... | A47J 31/461 |
| 2020/0297530 A1* | 9/2020 | Cohen | ................... | A61K 31/573 |
| 2020/0350047 A1* | 11/2020 | Spiro | ..................... | G16H 10/60 |
| 2020/0388361 A1* | 12/2020 | Richter | .................. | G16H 10/65 |
| 2021/0125696 A1* | 4/2021 | Liu | ......................... | G06N 20/00 |

OTHER PUBLICATIONS

"Using DNA Test Results, This Company Makes Customized Vitamins Specifically for You" Futurism Creative; Jun. 9, 2019; https://futurism.com/neoscope/dua-test-personaiized-vitamins retrieved Nov. 7, 2019.

"This Company Will Tell You Which Vitamins and Supplements to Take Base Don Your DNA" Sarah Buhr; Feb. 5, 2018; https://techcrunch.com/2018/02/05/this-company-will-tell-you-which-vitamins-and-supplements-to-take-based-on-your-dna/2018/02/05/this-company-will-tell-you-which-vitamins-and-supplements-to-take-based-on-your-dna/ retrieved Nov. 7, 2019.

* cited by examiner

METHOD OF AND SYSTEM FOR GENERATING A LONGEVITY ELEMENT AND AN INSTRUCTION SET FOR A LONGEVITY ELEMENT PLAN

CROSS-REFERENCE TO RELATED APPLICATIONS

This continuation-in-part application claims the benefit of priority of U.S. Non-Provisional Patent Application Ser. No. 16/699,407, filed on Nov. 29, 2019 and entitled "METHODS AND SYSTEMS FOR OPTIMIZING SUPPLEMENT DECISIONS", which is incorporated by reference herein in its entirety.

FIELD OF THE INVENTION

The present invention generally relates to the field of machine-learning. In particular, the present invention is directed to a system for generating a longevity element and an instruction set for a longevity element plan.

BACKGROUND

Design of systems for analysis of supplement data is often frustrated by the extreme complexity and variability of the subject matter between users. A vast multiplicity of factors to be considered is further complicated by a complex array of subtle, but crucial data. Worse still, user preferences may vary significantly between subjects, and in ways that can frustrate consistent application of supplement data to analytical techniques.

SUMMARY OF THE DISCLOSURE

In an aspect, a system for generating a longevity element and an instruction set for a longevity element plan, the system including at least a computing device, wherein the computing device is designed and configured to receive, from a user, a plurality of user-reported data, determine, using the at least an element of user-reported data and a first machine-learning process, a longevity element, calculate, using a longevity element and a second machine-learning process, a compensatory supplement, and generate, using the at least a longevity element and a third machine-learning process, an instruction set for a longevity element plan.

In another aspect, a method for generating a longevity element and an instruction set for a longevity element plan, the system including at least a computing device, wherein the computing device is designed and configured to receive, from a user, a plurality of user-reported data, determine, using the at least an element of user-reported data and a first machine-learning process, a longevity element, calculate, using a longevity element and a second machine-learning process, a compensatory supplement, and generate, using the at least a longevity element and a third machine-learning process, an instruction set for a longevity element plan.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a longevity element and an instruction set for a longevity element plan. In an embodiment, at least a computing device is designed and configured to receive, from a user, a plurality of user-reported data. Computing device uses a first machine-learning process and at least an element of user-reported data to determine a longevity element. Computing device calculates, using a longevity element and a second machine-learning process, a compensatory supplement. Computing device generates, using at least a longevity element and a third machine-learning process, an instruction set for a longevity element plan.

Figure 1:
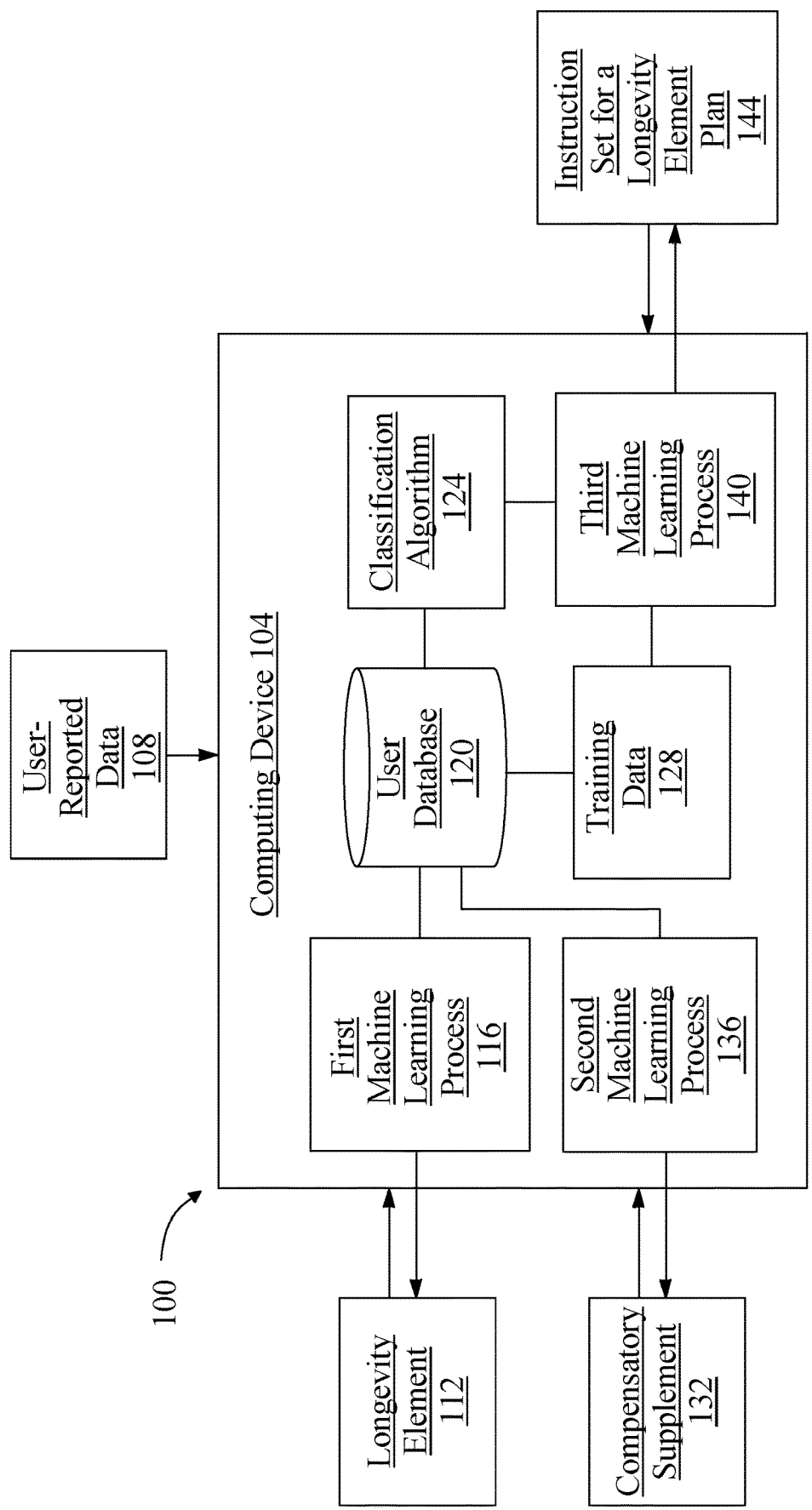
FIG. 1 is a block diagram of an exemplary embodiment of a system for determining user longevity element and longevity element instruction plan using a plurality of user-reported data and machine-learning.

Referring now to FIG. 1, an exemplary embodiment of a system 100 for generating a longevity element and an instruction set for a longevity element plan is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

Computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Referring to FIG. 1, computing device 104 is designed and configured to receive, from a user, at least an element of user-reported data 108. As described in this disclosure, "user-reported data," refers to information disclosed by a user to a system for the purpose of generating a longevity element and/or an instruction set for a longevity element 112. Longevity element may include, without limitation a personalized supplement dose. User-reported data may include at least a symptom, such as without limitation, being tired or lacking energy, medical information including drug allergies, current medications, and/or diagnoses, user preferences including food allergies, sensitivities, dietary restrictions, or the like, supplement quality, grade, availability, price; supplement delivery method and/or frequency of delivery. In non-limiting illustrative examples, user-reported data 108 may be a symptom, for instance feeling tired or lacking energy; user-reported data 108 may be an element of medical information such as a diagnosis of diabetes. A computing device 104 may be designed and configured to gather user-reported data 108 in a variety of ways, for instance without limitation, a web-based or mobile device application graphical user interface. Persons skilled in the art, upon reviewing the entirety of this disclosure, will be aware of various ways in which user-reported data may be input into a computing device 104 and may include, without limitation, user-reported data input into a computing device as described in U.S. Nonprovisional application Ser. No. 16/837,233, filed on Apr. 1, 2020, and entitled "METHODS AND SYSTEMS FOR GENERATING AN ALIMENTARY INSTRUCTION SET IDENTIFYING AN INDIVIDUAL PROGNOSTIC MITIGATION PLAN," the entirety of which is incorporated herein by reference.

Continuing in referring to FIG. 1, computing device 104 is to determine a longevity element 112. Determining the longevity element 112 may include training a first machine-learning process 116 using training data correlating user-reported data to supplement doses. A "longevity element", as used in this disclosure, may include an amount of a personalized supplement dose for a user to use. A longevity element 112 may be calculated as a function of a first machine-learning process 116 and at least an element of user-reported data 108 and/or an element of data retrieved from a database, as described below. Computing device may use at least an element of data that correlates a supplement to an element of user-reported data, from a database. Database may refer to a user database 120 which at least a computing device 104 may, alternatively or additionally, use to store and/or retrieve data, as described in further detail below. In non-limiting illustrative examples, a first machine-learning process 116 may input an element of user-reported data that is a diagnosis of diabetes, and may retrieve an element of data from a database that correlates user-reported incidence of diabetes to the efficacy of a ketogenic diet. In further non-limiting illustrative examples, a first machine-learning process 116 with these inputs may output a longevity element 112 that is a personalized supplement protein powder dose or omega fatty acid dose. In further non-limiting illustrative examples, a first machine-learning process 116 for generating a longevity element 112 may input two elements of user-reported data 108, for instance without limitation a medical condition of anemia and a preference for pharmaceutical grade supplements. A first machine-learning process 116 may use inputs to output a longevity element 112, as described in further detail below.

Continuing in reference to FIG. 1, first machine-learning process 116 may include at least a supervised machine-learning algorithm. Supervised machine-learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include an element of biological extraction 108 data as described above as inputs, taste indices as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine-learning algorithms that may be used to determine relation between inputs and outputs.

Supervised machine-learning processes may include classification algorithms 124, defined as processes whereby at least a computing device 104 derives, from training data, a model for sorting inputs into categories or bins of data to generate a classifier. Classification may be performed using, without limitation, linear classifiers such as without limitation logistic regression and/or naive Bayes classifiers, regression algorithms, nearest neighbor classifiers, support vector machines, decision trees, boosted trees, random forest classifiers, and/or neural network-based classifiers, such as supervised neural net algorithms. Supervised machine-learning processes may include, without limitation, machine-learning processes as described in U.S. Nonprovisional application Ser. No. 16/520,835, filed on Jul., 3, 2019, and entitled "METHODS AND SYSTEMS FOR ACHIEVING VIBRANT CONSTITUTION BASED ON USER INPUTS," the entirety of which is incorporated herein by reference. A "classifier," as described in this disclosure may refer to any machine-learning process output, as described above, that describes a category or subset of, without limitation, user-reported data, longevity element 112, compensatory supplement, and/or instruction set. A classifier may describe a subset of data that is useful for training a machine-learning process for outputting a machine-learning model, as described below. Supervised machine-learning may be performed by a regression-based machine learning method, such as linear and/or polynomial regression, or may be performed by training a neural network. Models may be generated using alternative or additional machine learning methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

Continuing in reference to FIG. 1, "training data," as used herein, is data containing correlations that a machine-learning process may use to model relationships between two or more categories of data elements. For instance, and without limitation, training data 124 may include a plurality of data entries, each entry representing a set of data elements that were recorded, received, and/or generated together; data elements may be correlated by shared existence in a given data entry, by proximity in a given data entry, or the like. Multiple data entries in training data 124 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories.

Multiple categories of data elements may be related in training data 124 according to various correlations; correlations may indicate causative and/or predictive links between categories of data elements, which may be modeled as relationships such as mathematical relationships by machine-learning processes as described in further detail below. Training data 124 may be formatted and/or organized by categories of data elements, for instance by associating data elements with one or more descriptors corresponding to categories of data elements. As a non-limiting example, training data 124 may include data entered in standardized forms by persons or processes, such that entry of a given data element in a given field in a form may be mapped to one or more descriptors of categories. Elements in training data 124 may be linked to descriptors of categories by tags, tokens, or other data elements; for instance, and without limitation, training data 124 may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data 124 may include one or more elements that are not categorized; that is, training data 124 may not be formatted or contain descriptors for some elements of data. Machine-learning algorithms and/or other processes may sort training data 124 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 124 to be made applicable for two or more distinct machine-learning algorithms as described in further detail below. Training data 124 used by computing device 104 may correlate any input data as described in this disclosure to any output data as described in this disclosure. As a non-limiting illustrative example, at least an element of user-reported data 108 of a longevity element 112 may correlate user reported data to a second longevity element 112. Additionally or alternatively, a classifier may describe a subset of useful data to be used as training data for outputting, for instance without limitation, a compensatory supplement. In non-limiting illustrative examples, a classifier used for training data 124 may be, for instance without limitation, generated as an output of a machine-learning process that describes a subset of data denoting expert submission retrieved from a database, past iterations of longevity element 112, instruction set, or the like, and/or subsets of user-reported data 108.

Still referring to FIG. 1, a "classifier," as used in this disclosure is a machine-learning model, such as a mathematical model, neural net, or program generated by a machine learning algorithm known as a "classification algorithm," as described above, that sorts inputs into categories or bins of data, outputting the categories or bins of data and/or labels associated therewith. For instance, without limitation, a Naïve Bayes classification algorithm 124 may generate classifiers by assigning class labels to problem instances, represented as vectors or element values. In non-limiting illustrative examples, class labels are drawn from a finite set, and classification algorithm 124 may include generating a family of algorithms that assume that the value of a particular element is independent of the value of any other element, given a class variable. In further non-limiting illustrative examples, a K-nearest neighbors (KNN) classification algorithm 124 may utilize feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. A classifier may be configured to output at least a datum that labels or otherwise identifies a set of data that are clustered together, found to be close under a distance metric as described below, or the like. Computing device 104 and/or another device may generate a classifier using a classification algorithm 124, defined by processes whereby a computing device 104 derives a classifier from training data, as described before.

Figure 2:
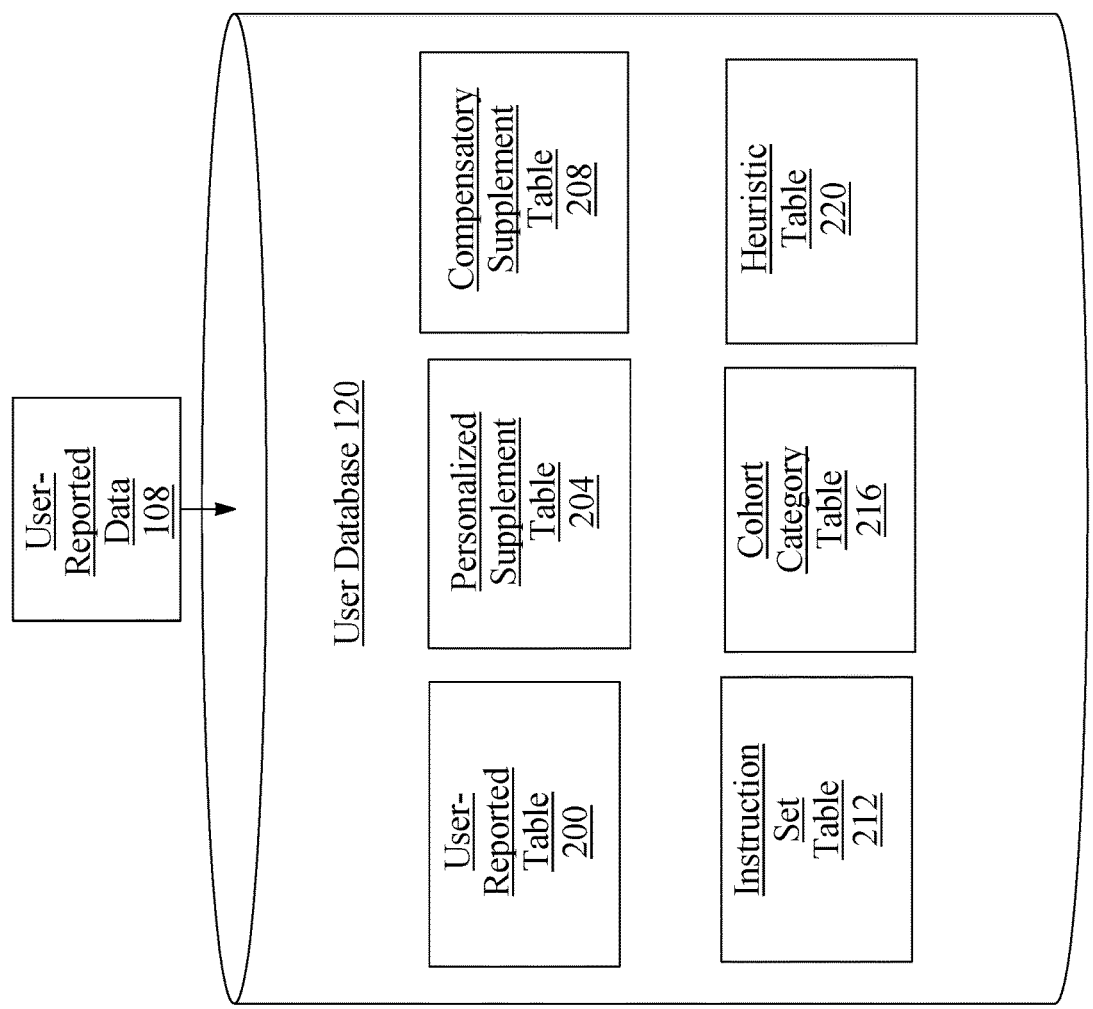
FIG. 2 is a block diagram of an exemplary embodiment of a user database.

Continuing in reference to FIG. 2, a non-limiting exemplary embodiment of a user database 120 is illustrated. Determinations by a machine-learning process may be stored and/or retrieved from the user database 120, for instance in non-limiting examples using a classifier. As a non-limiting example, user database 120 may organize data according to one or more personalized user-reported data tables 200. One or more database tables may be linked to one another by, for instance in a non-limiting example, common column values. For instance, a common column between two tables of user database 120 may include an identifier of a submission, such as a form entry, textual submission, research paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which data from one or more tables may be linked and/or related to data in one or more other tables.

Still referring to FIG. 2, in a non-limiting embodiment, one or more tables of a user database 120 may include, as a non-limiting example, a user-reported data table 200, which may include user-reported data 108 for use in determining a longevity element 112 and/or supplement instruction sets, entries indicating degrees of relevance to and/or efficacy in predicting compensatory supplement needs, and/or other elements of data computing device 104 and/or system 100 may use to determine usefulness and/or relevance of user-reported data 108 in determining longevity elements 112, compensatory supplement, and supplement plan instruction set as described in this disclosure. One or more tables may include, without limitation, a personalized supplement table 204, which may correlate user-reported data 108 and/or combinations thereof to one or more measures of a longevity element 112, such as dose or frequency of a personalized supplement for responding to a symptom. One or more tables may include, without limitation, a compensatory supplement table 208, which may contain a plurality of entries associating at least a longevity element 112 data with a relationship to a second nutrient in a user. One or more tables may include, without limitation, an instruction set table 212 which may contain one or more inputs identifying one or more categories of data, for instance dose, frequency, and delivery mode for a particular longevity element 112 used to address a particular symptom in users. One or more tables may include, without limitation, a cohort category table 216 which may contain one or more inputs identifying one or more categories of data, for instance physiological data, symptoms, longevity elements 112, or the like, with regard to which users having matching or similar data may be expected to have similar longevity elements 112 and/or compensatory supplements as a result of user-reported 108 data. One or more tables may include, without limitation, a heuristic table 220, which may include one or more inputs describing potential mathematical relationships between at least an element of user-reported data 108 and longevity element 112, compensatory supplement, and/or supplement plan, as described in further detail below.

Referring again to FIG. 1, computing device 104 is designed and configured to calculate, as a function of the longevity element 112 and a second machine-learning process, a compensatory supplement 132, as a function of longevity element 112. A "compensatory supplement," as used in this disclosure, is an amount of a compatible supplement to alleviate a side-effect that may arise in a user from taking a first longevity element 112, such as a personalized supplement. Computing device may retrieve at least a second element of data describing at least a side effect from a database, for instance using a particular longevity element 112 as a query. As a non-limiting illustrative example, a longevity element 112 may be a personalized supplement does of a daily zinc supplement for addressing sickle cell disease, and a compensatory supplement 132 may be an amount of daily copper supplement to counteract or balance any leeching or displacing of copper due to acute, increased zinc intake. In further non-limiting illustrative examples, the correlation between increased zinc uptake and copper displacement may be the second element of data denoting a side effect and may be retrieved from a database to calculate a compensatory supplement 132. In non-limiting embodiments, a second machine-learning process 136 may input a longevity element 112 and a second element of data retrieved from a database to output an amount of a compatible compensatory supplement 132. In non-limiting illustrative examples, an amount of a compensatory supplement 132 may be no amount. In further non-limiting illustrative examples, an amount of a compensatory supplement 132 to address a deficiency may be within the daily recommended allowance of what a user already receives without supplementation.

Second machine learning process 136 may be structured similarly to a first machine learning process, as described above. Second machine learning process 136 may use any process as described above, including without limitation regression and/or neural networks. Second machine learning process 136 may input a longevity element 112 and output a compensatory supplement 132 dose. Training data 128 may be implemented in any manner as described above for calculating a compensatory supplement 132. In non-limiting illustrative examples, training data 128 may correlate longevity element 112 inputs to compensatory supplement 132 outputs, user-reported data 108 data inputs to compensatory supplement 132 outputs, and/or expert submission inputs to compensatory supplement 132 outputs. Compensatory supplement 132 amounts calculated by a second machine learning process 136 may be stored and/or retrieved from a database for calculation of subsequent compensatory supplement 132 calculation, as described above.

Continuing in reference to FIG. 1, computing device 104 may be designed and configured to generate, using the at least a longevity element 112 and a third machine-learning process 140, an instruction set 144 for a longevity element plan. Generating instruction set 144 may include a plurality of user-reported data 108. As described in this disclosure, "an instruction set for a longevity element plan," refers to a series of numerical values that describe at least a longevity element 112 amount, an associated dosage, dosage form, frequency of dosage, delivery information for supplement, and/or a quality grade of supplement, with the goal of weaning a user off of a supplement, or the like, to address a user-reported symptom. An instruction set 144 may include a compensatory supplement 132 amount, an associated dosage, dosage form, frequency of dosage, delivery information for supplement, and/or a quality grade of compensatory supplement 132, with the goal of weaning a user off of the compensatory supplement 132 to address a first user-reported symptom. In non-limiting illustrative examples, dosage may refer to, for instance without limitation, a mg/kg bodyweight amount; dosage form may refer to the physical state of the supplement, for instance without limitation, pill form, powder form, liquid form, or the like; frequency of dosage may refer to a recommended time course of taking the supplement, for instance without limitation, once daily; delivery information for supplement may refer to, for instance without limitation, a 30-day supply shipped monthly or a user-selected timeframe; quality grade of supplement may refer to, without limitation, feed-grade, food-grade, or pharmaceutical-grade quality supplement. As used in this disclosure, "weaning a user off a supplement," refers to gradually decreasing a supplement dosage and/or frequency until a user-reported symptom, disease, ailment, or the like, has been addressed. In non-limiting illustrative examples, an instruction set for a personalized supplement plan 144 may include numerical values of time and dosage to accomplish weaning a user off a longevity element 112 and/or a compensatory supplement 132 of a plurality of supplements, foods, medications, or the like. In further non-limiting illustrative examples, an instruction set for a longevity element plan 144 may describe delivery duration that reflects a complete dosage frequency for weaning a user off a supplement. A third machine-learning process 140 may be generated by training a machine-learning process using training data 128, as described above. In non-limiting illustrative examples, training data 128 to generate a third machine-learning process 140 may include, without limitation, a plurality of user-reported data, including a symptom, a dosage form preference, a dosage frequency preference, a quality preference, and/or a delivery method. Additionally or alternatively, training data 128 to generate a third machine-learning process 140 may include, without limitation, a subset of user-reported data 108 that is described or categorized by a classifier, as described above. In non-limiting illustrative examples, a machine-learning process may be trained with a longevity element 112 of a plurality of longevity elements 112 and a compensatory supplement 132 of a plurality of compensatory supplements to output a third machine-learning process 140 for generating an instruction set for a longevity element plan 144. In further non-limiting illustrative examples, a third machine-learning process 140 may be trained with a subset of user-reported data 108 and used with a machine-learning process inputting a longevity element 112 and a compensatory supplement 132 to output an instruction set for a longevity element plan 144 that may describe a longevity element 112 amount, a compensatory supplement 132 amount, a dosage for each, dosage form, a dosage frequency for each, a quality grade for each supplement, and a delivery method for each supplement.

Continuing in reference to FIG. 1, generating an instruction set for a longevity element plan 144 using a third machine-learning process further comprises training a third machine-learning process with training data, wherein training data refers to a plurality of user-reported entries categorized by a classifier. In non-limiting illustrative examples, a classifier may describe a subset of user-reported data 108, longevity element 112, and/or compensatory supplement 132 that may be useful to generating an instruction set for a longevity element plan 144, as described before.

Figure 3:
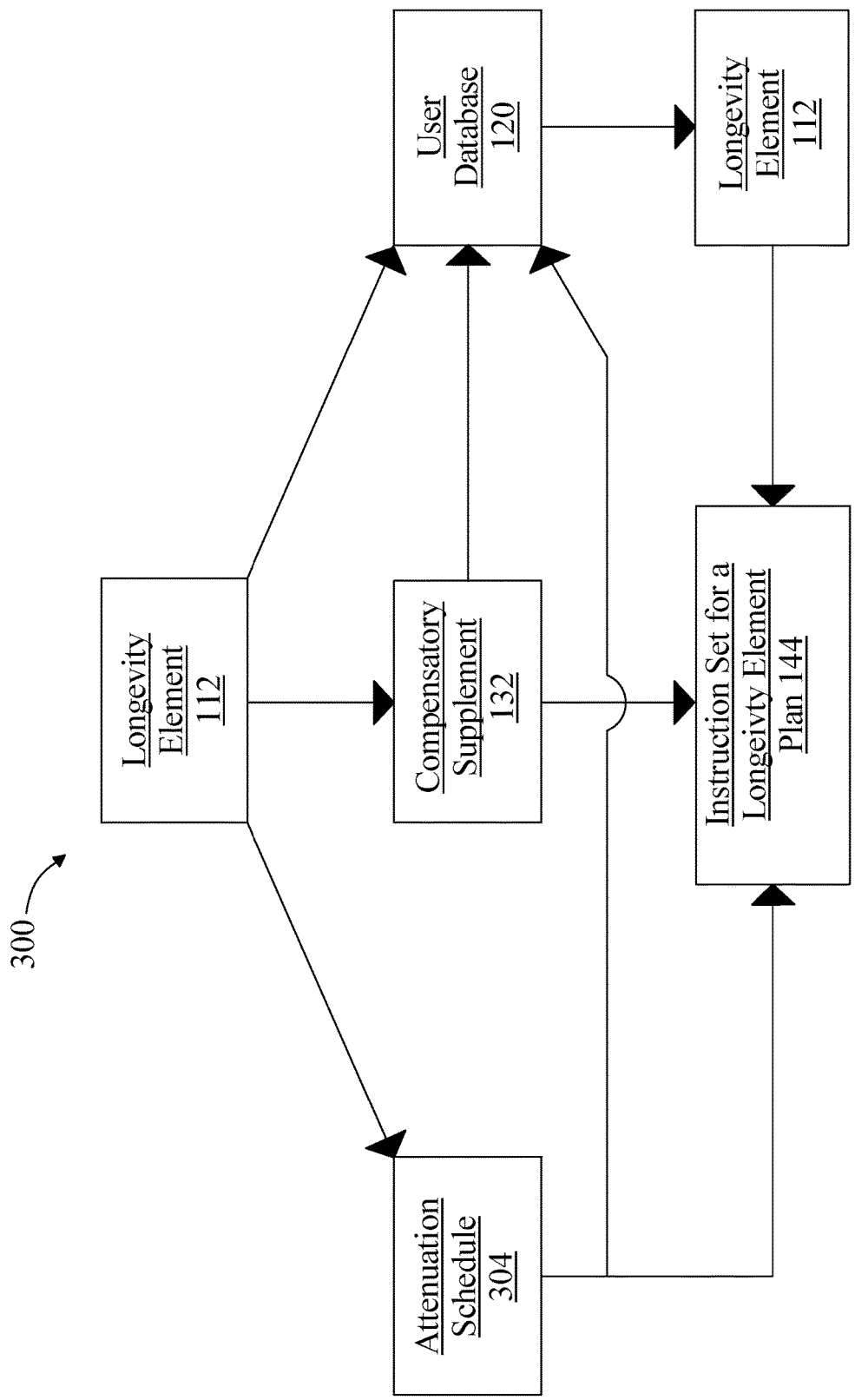
FIG. 3 is a block diagram of an exemplary embodiment of an instruction set for a longevity element plan.

Referring now to FIG. 3, an exemplary embodiment of the outputs comprising an instruction set for a longevity element plan 300 is illustrated, wherein an instruction set for a longevity element plan 144 may include an attenuation schedule 304 for weaning a user off a first longevity element 112. An "attenuation schedule," as described in this disclosure refers to a numerical value and/or set of values described by a matrix, table, vector, function, or the like that describe a dose, dose frequency, and time period of a longevity element 112 to address at least a symptom of a user. In non-limiting illustrative examples, an attenuation schedule 304 may describe a supplement dose, dose frequency, and period with the long-term goal of eliminating the need of a supplement.

Continuing in reference to FIG. 3, attenuation schedule 304 may be generated as an output of a fourth machine-learning process using a machine-learning model trained with training data that corresponds to at least a longevity element 112, as described above. Training data for generating an attenuation schedule 304 may be selected using a classifier classifying training data entries to user as described above. Training data for fourth machine learning process may be data describing supplement dosage and frequency. In non-limiting illustrative examples, attenuation schedule 304 may be output by a fourth machine learning process. Alternatively or additionally, attenuation schedule 304 may be added to instruction set 144.

Still referring to FIG. 3, computing device may receive an identified side-effect. An identified side-effect may describe any unintended and/or intended consequence of using a longevity element 112, or a compensatory supplement 132 as received from user, a medical professional, or the like, for instance as detected by such persons after user has begun taking longevity element 112. An identified side-effect 304 may be used by computing device 104 as a function of second machine-learning process 136 to output a compensatory supplement 132, which may be included as part of an instruction set 144, for instance as described above. Alternatively or additionally, computing device 104 may generate a new instruction set 144 canceling longevity element 112 and replacing it with an alternative supplement dose. Alternative supplement dose may be identified using first machine-learning process 116, as described above. Generation of a longevity element 112 and/or substitute dose by first machine-learning process 116 may be stored in a user database 120 to be used as an input for a second longevity element 112. Substitute doses may be iteratively generated from user database 120 and/or first machine-learning process 116; updated user data may include to any longevity element 112, side-effect 304, compensatory supplement 112. In non-limiting illustrative examples, an instruction set for a longevity element plan 144 may include a second and/or substitute longevity element 112 of a plurality of longevity elements 112.

Figure 4:
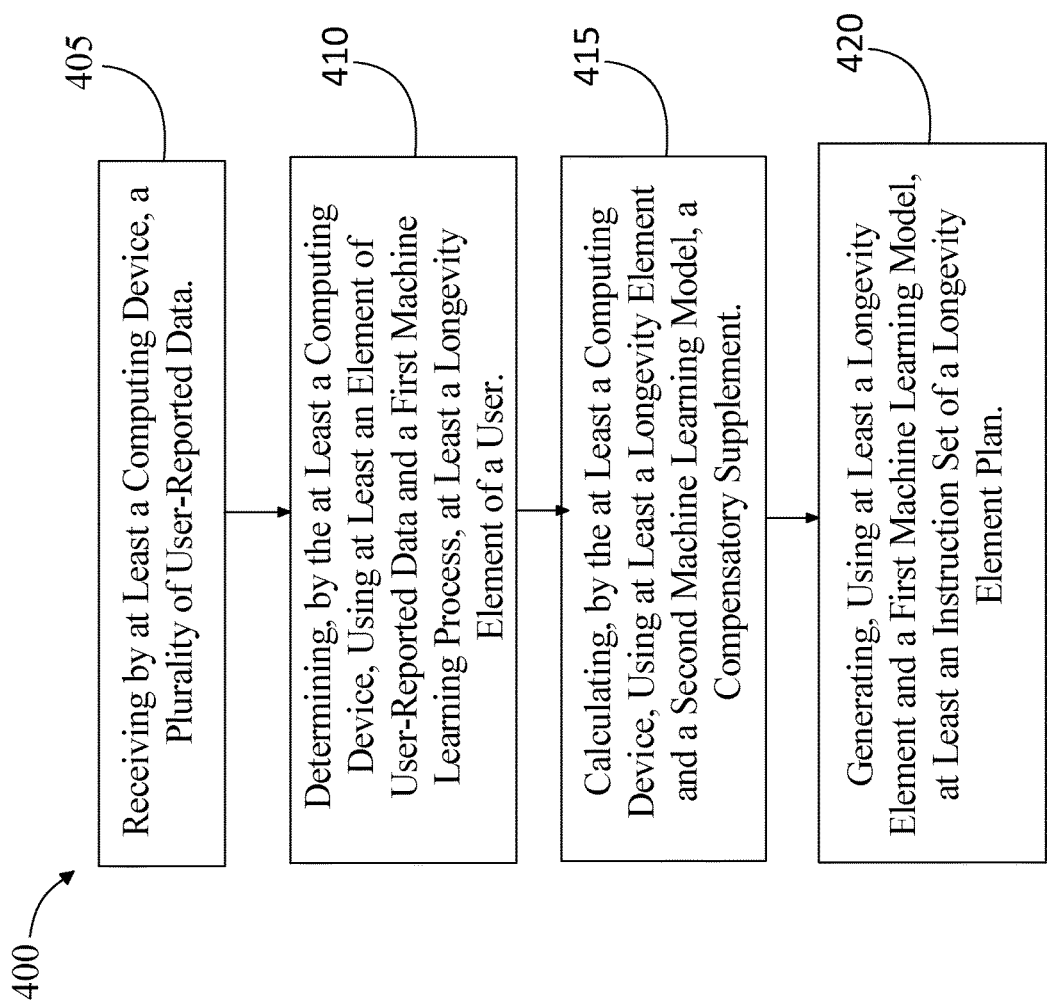
FIG. 4 is a flowchart describing an exemplary embodiment of a method using the system of the invention.

Referring now to FIG. 4, an exemplary embodiment of a method 400 of generating a longevity element 112 and an instruction set for a longevity element plan 144 using a machine-learning is illustrated. At step 405, method 400 includes receiving by the at least a computing device 104, a plurality of user-reported data 108; this may be implemented, without limitation, as described above in reference to FIGS. 1-2. At step 410, method 400 includes determining by the at least a computing device 104 using at least an element of user-reported data 108 and a first machine-learning process 116, a longevity element 112 of a user; this may be implemented, without limitation, as described above in reference to FIGS. 1-2. Determining an amount of a longevity element 112 using a first machine-learning process 116 may include receiving at least an element of user-reported data 108, retrieving at least an element of data that correlates a supplement to an element of user-reported data 108, from a database, and calculating, using at least an element of user-reported data a correlation to a supplement and a first machine-learning process 116, an amount of a longevity element 112 to address an element of user-reported data 108. At step 415, method 400 includes calculating, by the at least a computing device 104, using at least a longevity element 112 and a second machine-learning process 136, a compensatory supplement 132; this may be implemented, without limitation, as described above in reference to FIGS. 1-2. Calculating a compensatory supplement 132 may include a longevity element 112, retrieving at least a second element of data from a database, wherein a second element of data is at least a side-effect 304 from a first longevity element 112, and calculating, a compensatory supplement 132 amount to alleviate a side-effect 304 of the longevity element 112. At step 420, method 400 includes generating, using at least a longevity element 112 and a third machine-learning process 140, at least an instruction set for a longevity element plan 144; this may be implemented, without limitation, as described above in reference to FIGS. 1-2. Generating the instruction set 144 may include using a plurality of user-reported data 108. Generating the instruction set may include training the machine-learning model as a function of the plurality of user-reported entries. The plurality of user-reported data 108 may include at least a symptom, dosage form preference, dosage frequency preference, quality preference, and delivery method. Instruction set may include calculating an attenuation schedule for a longevity element 112. It will be understood by those skilled in the art, after reviewing the disclosure in its entirety, the various ways data may be input in a computing device 104 and the various ways outputs may be communicated by a computing device 104 to a user for all steps described above.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 5:
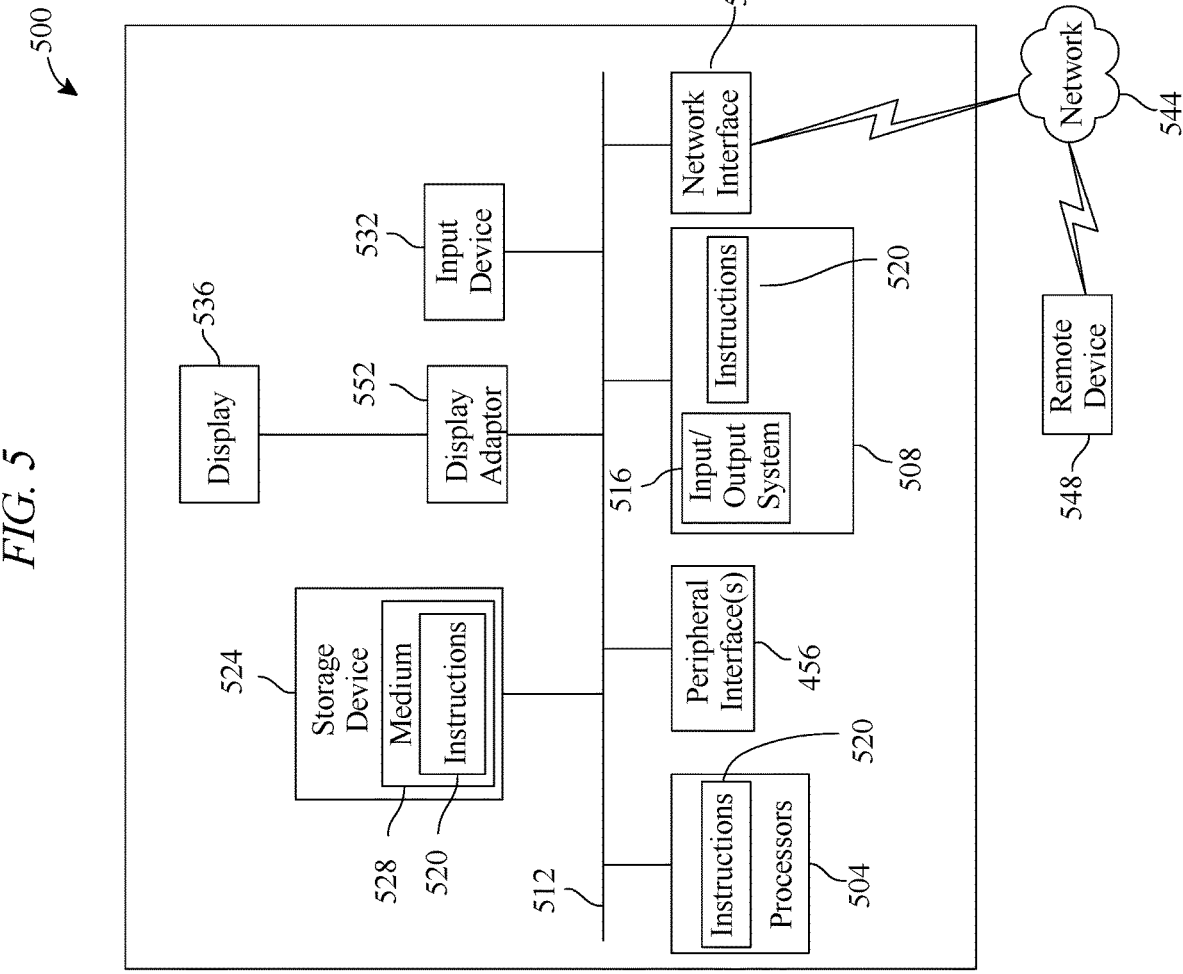
FIG. 5 is a block diagram of a computing system that can be used to implement any one or more of the methodologies disclosed herein and any one or more portions thereof.

FIG. 5 shows a diagrammatic representation of one embodiment of a computing device in the exemplary form of a computer system 500 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 500 includes a processor 504 and a memory 508 that communicate with each other, and with other components, via a bus 512. Bus 512 may include any of several types of bus structures including, but not limited to, a memory bus, a memory controller, a peripheral bus, a local bus, and any combinations thereof, using any of a variety of bus architectures.

Processor 504 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 504 may be organized according to Von Neumann and/or Harvard architecture as a non-limiting example. Processor 504 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 508 may include various components (e.g., machine-readable media) including, but not limited to, a random-access memory component, a read only component, and any combinations thereof. In one example, a basic input/output system 516 (BIOS), including basic routines that help to transfer information between elements within computer system 500, such as during start-up, may be stored in memory 508. Memory 508 may also include (e.g., stored on one or more machine-readable media) instructions (e.g., software) 520 embodying any one or more of the aspects and/or methodologies of the present disclosure. In another example, memory 508 may further include any number of program modules including, but not limited to, an operating system, one or more application programs, other program modules, program data, and any combinations thereof.

Computer system 500 may also include a storage device 524. Examples of a storage device (e.g., storage device 524) include, but are not limited to, a hard disk drive, a magnetic disk drive, an optical disc drive in combination with an optical medium, a solid-state memory device, and any combinations thereof. Storage device 524 may be connected to bus 512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 524 (or one or more components thereof) may be removably interfaced with computer system 500 (e.g., via an external port connector (not shown)). Particularly, storage device 524 and an associated machine-readable medium 528 may provide nonvolatile and/or volatile storage of machine-readable instructions, data structures, program modules, and/or other data for computer system 500. In one example, software 520 may reside, completely or partially, within machine-readable medium 528. In another example, software 520 may reside, completely or partially, within processor 504.

Computer system 500 may also include an input device 532. In one example, a user of computer system 500 may enter commands and/or other information into computer system 500 via input device 532. Examples of an input device 532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 532 may be interfaced to bus 512 via any of a variety of interfaces (not shown) including, but not limited to, a serial interface, a parallel interface, a game port, a USB interface, a FIREWIRE interface, a direct interface to bus 512, and any combinations thereof. Input device 532 may include a touch screen interface that may be a part of or separate from display 536, discussed further below. Input device 532 may be utilized as a user selection device for selecting one or more graphical representations in a graphical interface as described above.

A user may also input commands and/or other information to computer system 500 via storage device 524 (e.g., a removable disk drive, a flash drive, etc.) and/or network interface device 540. A network interface device, such as network interface device 540, may be utilized for connecting computer system 500 to one or more of a variety of networks, such as network 544, and one or more remote devices 548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 544, may employ a wired and/or a wireless mode of communication. In general, any network topology may be used. Information (e.g., data, software 520, etc.) may be communicated to and/or from computer system 500 via network interface device 540.

Computer system 500 may further include a video display adapter 552 for communicating a displayable image to a display device, such as display device 536. Examples of a display device include, but are not limited to, a liquid crystal display (LCD), a cathode ray tube (CRT), a plasma display, a light emitting diode (LED) display, and any combinations thereof. Display adapter 552 and display device 536 may be utilized in combination with processor 504 to provide graphical representations of aspects of the present disclosure. In addition to a display device, computer system 500 may include one or more other peripheral output devices including, but not limited to, an audio speaker, a printer, and any combinations thereof. Such peripheral output devices may be connected to bus 512 via a peripheral interface 556. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a longevity element and an instruction set for a longevity element plan, the system comprising:
at least a computing device, wherein the computing device is designed and configured to:
receive, from a user, a plurality of user-reported data;
determine a longevity element, wherein determining the longevity element further comprises:
receiving training data correlating user-reported data to supplement doses;
training a first machine-learning process as a function of the training data; and
determining the longevity element as a function of the first machine-learning process;
calculate, as a function of the longevity element and a second machine-learning process, a compensatory supplement, wherein the second machine-learning process is trained with training data correlating longevity elements to compensatory supplements, and wherein the second machine-learning model is configured to input the longevity element and output the compensatory supplement;
generate, as a function of the at least a longevity element and a third machine-learning process, an instruction set corresponding to a longevity element plan, wherein the longevity element plan comprises a delivery duration for weaning a user off a supplement.

2. The system of claim 1, wherein determining an amount of a longevity element using a first machine-learning process further comprises:
receiving at least an element of user-reported data;
retrieving at least an element of data that correlates a supplement to an element of user-reported data, from a database; and
calculating, using at least an element of user-reported data a correlation to a supplement and a first machine-learning process, an amount of a longevity element to address an element of user-reported data.

3. The system of claim 1, wherein calculating a compensatory supplement further comprises:
retrieving at least a second element of data from a database, wherein a second element of data is at least a side-effect from a first longevity element; and
calculating, a compensatory supplement amount to alleviate a side-effect of the longevity element.

4. The system of claim 1, wherein generating the instruction set for a longevity element plan further comprises generating the instruction set as a function of a plurality of user-reported data.

5. The system of claim 4, wherein generating the instruction set further comprises training a machine-learning model as a function of the plurality of user-reported entries.

6. The system of claim 4, wherein the plurality of user-reported data further comprises at least a symptom.

7. The system of claim 4, wherein the plurality of user-reported data further comprises at least a dosage form preference and at least a dosage frequency preference.

8. The system of claim 4, wherein the plurality of user-reported data further comprises a quality preference.

9. The system of claim 4, wherein the plurality of user-reported data further comprises a delivery method.

10. The system of claim 4, wherein generating the instruction set further comprises calculating an attenuation schedule for a longevity element.

11. A method for generating a longevity element and an instruction set for a longevity element plan, the method comprising:
at least a computing device, wherein the computing device is designed and configured for:
receiving, from a user, a plurality of user-reported data;
determining, using the at least an element of user-reported data and a first machine-learning process, a longevity element;
calculating, using a longevity element, and a second machine-learning process, a compensatory supplement, wherein the second machine-learning process is trained with training data correlating longevity elements to compensatory supplements, and wherein the second machine-learning model is configured to input the longevity element and output the compensatory supplement;
generate, using the at least a longevity element and a third machine-learning process, an instruction set for a longevity element plan, wherein the longevity element plan comprises a delivery duration for weaning a user off a supplement.

12. The method of claim 11, wherein determining an amount of a longevity element using a first machine-learning process further comprises:
receiving at least an element of user-reported data;
retrieving at least an element of data that correlates a supplement to an element of user-reported data, from a database; and
calculating, using at least an element of user-reported data a correlation to a supplement and a first machine-learning process, an amount of a longevity element to address an element of user-reported data.

13. The method of claim 11, wherein calculating a compensatory supplement further comprises:
a longevity element; and
retrieving at least a second element of data from a database, wherein a second element of data is at least a side-effect from a first longevity element; and
calculating, a compensatory supplement amount to alleviate a side-effect of the longevity element.

14. The method of claim 11, wherein generating the instruction set for a longevity element plan further comprises generating the instruction set as a function of a plurality of user-reported data.

15. The method of claim 14, wherein generating the instruction set longevity element plan further comprises training the machine-learning model with as a function of the plurality of user-reported entries.

16. The method of claim 14, wherein the plurality of user-reported data further comprises at least a symptom.

17. The method of claim 14, wherein the plurality of user-reported data further comprises at least a dosage form preference and at least a dosage frequency preference.

18. The method of claim 14, wherein the plurality of user-reported data further comprises a quality preference.

19. The method of claim 14, wherein the plurality of user-reported data further comprises a delivery method.

20. The method of claim 14, generating the instruction set further comprises calculating an attenuation schedule for a longevity element.

* * * * *